(12) United States Patent
Szypka

(10) Patent No.: US 9,248,059 B2
(45) Date of Patent: *Feb. 2, 2016

(54) ANIMAL INCONTINENCE DEVICE

(71) Applicant: Andrew J. Szypka, Curtice, OH (US)

(72) Inventor: Andrew J. Szypka, Curtice, OH (US)

(73) Assignee: PRINCIPLE BUSINESS ENTERPRISES, INC., Dunbridge, OH (US)

( * ) Notice: Subject to any disclaimer, the term of this patent is extended or adjusted under 35 U.S.C. 154(b) by 128 days.

This patent is subject to a terminal disclaimer.

(21) Appl. No.: 13/622,692

(22) Filed: Sep. 19, 2012

(65) Prior Publication Data

US 2013/0014702 A1  Jan. 17, 2013

Related U.S. Application Data

(63) Continuation of application No. 10/545,713, filed as application No. PCT/US2005/024078 on Jul. 7, 2005, now Pat. No. 8,334,424.

(60) Provisional application No. 60/638,462, filed on Dec. 22, 2004.

(51) Int. Cl.
| | |
|---|---|
| A61F 13/15 | (2006.01) |
| A61F 13/511 | (2006.01) |
| A61F 13/514 | (2006.01) |
| A61F 13/515 | (2006.01) |
| A61F 13/53 | (2006.01) |
| A61F 13/539 | (2006.01) |
| A61F 13/20 | (2006.01) |

(52) U.S. Cl.
CPC ............ *A61F 13/511* (2013.01); *A61F 13/515* (2013.01); *A61F 13/51401* (2013.01); *A61F 13/53* (2013.01); *A61F 13/539* (2013.01); *A61F 2013/530481* (2013.01)

(58) Field of Classification Search
CPC ................................. A61F 13/15; A61F 13/20
USPC ..................... 604/358, 367, 385.23, 386, 387
See application file for complete search history.

(56) References Cited

U.S. PATENT DOCUMENTS

| | | |
|---|---|---|
| 3,626,899 A | 12/1971 | Spellman |
| 3,697,623 A | 10/1972 | Eimers |
| 4,055,184 A | 10/1977 | Karami |
| 4,260,443 A | 4/1981 | Lindsay et al. |
| 4,551,191 A | 11/1985 | Kock et al. |
| 4,761,322 A | 8/1988 | Raley |
| 4,774,907 A | 10/1988 | Yananton |
| 4,800,677 A | 1/1989 | Mack |
| 5,226,386 A | 7/1993 | Thoma |
| 5,429,629 A | 7/1995 | Latimer et al. |
| 5,464,402 A | 11/1995 | Zajaczkowski |
| 5,601,542 A | 2/1997 | Melius et al. |
| 5,630,376 A * | 5/1997 | Ochi et al. ............... 119/169 |
| 5,715,772 A | 2/1998 | Kamrath et al. |
| 6,096,067 A | 8/2000 | Cramer et al. |
| 6,129,717 A | 10/2000 | Fujioka et al. |
| 6,140,550 A | 10/2000 | Beihoffer et al. |
| 6,227,145 B1 | 5/2001 | Miyamoto et al. |
| 6,244,216 B1 * | 6/2001 | Ochi ........................ 119/171 |
| 6,295,658 B1 | 10/2001 | Jenkins |
| 6,336,935 B1 | 1/2002 | Davis et al. |
| 6,369,290 B1 * | 4/2002 | Glaug et al. ............... 604/359 |
| 6,575,952 B2 * | 6/2003 | Kirk et al. ................. 604/386 |
| 6,582,413 B2 | 6/2003 | Krautkramer et al. |
| 6,582,416 B2 | 6/2003 | Tapper |
| 6,635,799 B1 | 10/2003 | Osborn, III et al. |
| 6,706,946 B1 | 3/2004 | Lankhof et al. |
| 6,911,253 B2 | 6/2005 | Iwasa et al. |
| 2001/0044611 A1 | 11/2001 | Noda et al. |
| 2003/0082966 A1 | 5/2003 | Menday et al. |
| 2004/0033750 A1 | 2/2004 | Everett et al. |
| 2004/0082246 A1 | 4/2004 | Watanabe et al. |

* cited by examiner

*Primary Examiner* — Tatyana Zalukaeva
*Assistant Examiner* — Ilya Treyger
(74) *Attorney, Agent, or Firm* — Fraser Clemens Martin & Miller LLC; Jacob M. Ward

(57) ABSTRACT

An animal incontinence device comprises a base layer of a liquid-impervious polymer film, an intermediate absorbent layer comprising superabsorbent polymer particles intermediate a plurality of layers of tissue, and a top layer comprising a porous, hydrophilic, woven or non-woven polymer fiber mat.

12 Claims, No Drawings

ANIMAL INCONTINENCE DEVICE

CROSS-REFERENCE TO RELATED APPLICATIONS

This application is a continuation of U.S. patent application Ser. No. 10/545,713, filed Aug. 12, 2005, which in turn is a National Stage of International Application No. PCT/US05/24078, filed Jul. 7, 2005, which in turn claims the benefit of U.S. provisional patent application Ser. No. 60/638,462, filed Dec. 22, 2004.

FIELD OF THE INVENTION

The present invention relates generally to an animal incontinence device. More particularly, the invention is directed to a multi-layered floor pad useful for absorbing animal urine.

BACKGROUND OF THE INVENTION

Devices for dealing with animal incontinence are known in the art. Such devices generally contain an absorbent layer of fibers or cellulose pulp. These devices are ineffective for absorbing and immobilizing animal urine, so that it is not squeezed out of the device and tracked by the animal over the floor.

It would be desirable to prepare an improved animal incontinence device that would absorb, contain, and immobilize the animal's urine.

SUMMARY OF THE INVENTION

Accordant with the present invention, an animal incontinence device, that immobilizes the animal's urine, has surprisingly been discovered. It comprises a base layer of a liquid-impervious polymer film, an intermediate absorbent layer comprising superabsorbent polymer (SAP) particles intermediate a plurality of layers of tissue, and a top layer comprising a porous, hydrophilic, woven or non-woven polymer fiber mat. At least the base and top layers are sealed together at their edges, to encapsulate the intermediate layer containing the SAP.

The animal incontinence device according to the present invention is particularly useful for absorbing the urine of an incontinent animal, to keep the surrounding premises free from tracked urine.

DETAILED DESCRIPTION OF THE PREFERRED EMBODIMENT

The present invention comprises a base layer of a liquid-impervious polymer film, an intermediate absorbent layer comprising superabsorbent polymer (SAP) particles intermediate a plurality of layers of tissue, and a top layer comprising a porous, hydrophilic, woven or non-woven polymer fiber mat. At least the base and top layers are sealed together at their edges, to encapsulate the intermediate layer containing the SAP.

The base layer may comprise any liquid-impervious polymer film. Polymers from which the base layer may be prepared include, but are not necessarily limited to, a polyethylene, polypropylene, polystyrene, polyacrylate, polymethacrylate, polyvinyl chloride, polyacrylonitrile, polyvinyl acetate, polyvinyl alcohol, polyolefin, polyester, polycarbonate, polyether, polyamide, and the like, as well as derivatives, blends, and copolymers thereof. Preferred base layers comprise a polyethylene or a polypropylene. A particularly preferred polyethylene or polypropylene base layer has a thickness ranging from about 0.6 to about 1.0 mil. Such polymer films are well known and commercially available.

The intermediate layer, according to the present invention, comprises superabsorbent polymer (SAP) particles intermediate a plurality of layers of tissue. Superabsorbent polymers are cross-linked networks of flexible polymer chains. The most efficient water absorbers are polymer networks that carry dissociated ionic functional groups. SAP's work by diffusion on the molecular level. Water diffuses into the particles of superabsorbent polymer, and SAP particles swell to accommodate the additional water molecules. Because the polymer molecules are cross-linked, they do not dissolve in the absorbed liquid. The SAP particles are placed intermediate a plurality of layers of tissue. Any number of layers of tissue equal to or greater than two and up to about ten is operable according to the present invention. Preferably, the SAP particles are bonded between two layers of single-ply cellulosic tissue. The SAP particles may be bonded and secured to the tissue plies by the application of heat, pressure, and/or a bonding agent (e.g., a polyolefin powder adhesive, a hot melt adhesive, a water based or non-water based liquid adhesive, or the like).

Preferably, the intermediate layer has a dry core with excellent SAP particle distribution and uniformity, with a high SAP-to-total-intermediate-layer weight ratio of from about forty percent (40%) to about fifty percent (50%). A preferred intermediate layer containing superabsorbent polymer may be obtained from Gelok International Corporation of Dunbridge, Ohio. A particularly preferred intermediate layer may be obtained from Gelok under the product designation "2040 SS."

The top layer, according to the present invention, comprises a porous, hydrophilic, woven or non-woven polymer fiber mat. The top layer may comprise any monolithic, flexible, porous material including, but not necessarily limited to, a non-woven or woven textile cloth or mat, a sponge material, or the like. A preferred non-woven substrate generally comprises an adhesively bonded fibrous or filamentous material having a web or carded fiber structure, or a mat in which the fibers are distributed either in a random fashion or in a substantially aligned manner. The fibers or filaments generally comprise natural materials, e.g., fibers or filaments of synthetic materials, e.g., polyolefins, polyesters, rayon, cellulose esters, polyvinyl derivatives, polyamides, and the like, as well as combinations thereof. The thickness of the top layer may vary over wide limits. A particularly preferred top layer comprises a porous, hydrophilic, spun bonded polypropylene, having a weight from about 12 to about 13.5 gsm. Such top layer materials are well known in the industry, and are commercially available.

At least the base and top layers are sealed together at their peripheral edges, to encapsulate the intermediate layer containing the SAP. The base and top layers may be heat sealed together by, for example, the application of a heated and nip rollers to the edges of the assembled multi-layered structure. Alternatively, the top and base layers may be adhered at their edges, by the application of a hot melt or other appropriate adhesive intermediate the perimeters of the top and base layers. Thus, the intermediate layer containing the SAP is effectively encapsulated between the top and base layers.

In an alternative embodiment, the base layer may be larger in area than the top layer, so that the base layer may be folded up and over the distal edges of the top layer before sealing the assemblage. This may improve the fluid retention of the inventive device.

It is observed that the animal incontinence device according to the present invention, utilizing the intermediate layer containing the superabsorbent polymer, has a thickness equal to about one-third of the prior art product. This is an important feature when contemplating shipping, storage, and use of the device.

The animal incontinence device according to the present invention may additionally comprise adjuvants for enhanced performance; such as for example, fragrances or neutralizers like sodium bicarbonate. These materials may be applied to any of the layers of the device, or may be added neat to the assemblage before the top and base layers are sealed.

The invention is more easily comprehended by reference to specific embodiments recited hereinabove, which are representative of the invention. It must be understood, however, that the specific embodiments are provided only for the purpose of illustration, and that the invention may be practiced otherwise than as specifically illustrated without departing from its spirit and scope.

What is claimed is:

1. An animal incontinence device, comprising:
   a base layer of a liquid-impervious polymer film;
   an intermediate absorbent layer consisting of superabsorbent polymer particles, an adhesive, and at least one adjuvant disposed intermediate two layers of single-ply cellulosic tissue; and
   a top layer comprising a porous, hydrophilic, non-woven spun bonded polymer fiber mat;
   wherein the base and top layers are sealed together with an adhesive and encapsulate the intermediate absorbent layer with the superabsorbent polymer particles, the base layer larger in area than the top layer so that at least one of the peripheral edges of the base layer is folded up and over the peripheral edges of the top layer, the adhesive disposed intermediate the perimeters of the top and base layers to seal the base and top layers directly together at their peripheral edges.

2. The animal incontinence device according to claim 1, wherein the base layer comprises polyethylene, polypropylene, polystyrene, polyacrylate, polymethacrylate, polyvinyl chloride, polyacrylonitrile, polyvinyl acetate, polyvinyl alcohol, polyolefin, polyester, polycarbonate, polyether, polyamide, or a derivative, blend, or copolymer thereof.

3. The animal incontinence device according to claim 1, wherein the base layer comprises polyethylene or a polypropylene.

4. The animal incontinence device according to claim 1, wherein the base layer has a thickness ranging from about 0.6 to about 1.0 mil.

5. The animal incontinence device according to claim 1, wherein the intermediate layer comprises from two to ten layers of tissue.

6. The animal incontinence device according to claim 1, wherein the intermediate layer comprises from about 40 to about 50 weight percent superabsorbent particles.

7. The animal incontinence device according to claim 1, wherein the top layer fibers comprise polyolefin, polyester, rayon, cellulose ester, a polyvinyl derivative, polyamide, or a combination thereof.

8. The animal incontinence device according to claim 1, wherein the top layer comprises a porous, hydrophilic, spun bonded polypropylene, having a weight from about 12 to about 13.5 gsm.

9. The animal incontinence device according to claim 1, wherein the at least one adjuvant includes a fragrance and a neutralizer.

10. An absorbent device, comprising:
    a base layer;
    an intermediate absorbent layer consisting of superabsorbent polymer particles, an adhesive, and at least one adjuvant disposed intermediate two layers of single-ply cellulosic tissue; and
    a top layer comprising a porous, hydrophilic, non-woven spun bonded polymer fiber mat,
    wherein the base and top layers are sealed directly together with an adhesive and encapsulate the intermediate absorbent layer with the superabsorbent polymer particles.

11. The absorbent device according to claim 10, wherein the top layer comprises a porous, hydrophilic, spun bonded polypropylene, having a weight from about 12 to about 13.5 gsm.

12. An absorbent device, comprising:
    a base layer;
    an intermediate absorbent layer consisting of superabsorbent polymer particles and at least one adjuvant disposed intermediate two layers of single-ply cellulosic tissue; and
    a top layer comprising a porous, hydrophilic, non-woven spun bonded polymer fiber mat,
    wherein the base and top layers are sealed directly together with an adhesive and
    encapsulate the intermediate absorbent layer with the superabsorbent polymer particles.

* * * * *